United States Patent [19]
Menchen et al.

[11] Patent Number: 5,885,778
[45] Date of Patent: *Mar. 23, 1999

[54] 4, 7-DICHLOROFLUORESCEIN DYES AS MOLECULAR PROBES

[75] Inventors: Steven M. Menchen, Fremont; Linda G. Lee, Palo Alto; Charles R. Connell, Redwood City; N. Davis Hershey, San Carlos; Vergine Chakerian, San Mateo; Sam L. Woo, Redwood City; Steven Fung, Palo Alto, all of Calif.

[73] Assignee: The Perkin-Elmer Corporation, Foster City, Calif.

[ * ] Notice: The term of this patent shall not extend beyond the expiration date of Pat. No. 5,188,934.

[21] Appl. No.: 905,855

[22] Filed: Aug. 4, 1997

Related U.S. Application Data

[63] Continuation of Ser. No. 400,780, Mar. 8, 1995, Pat. No. 5,654,442, which is a continuation of Ser. No. 939,813, Sep. 3, 1992, abandoned, which is a continuation-in-part of Ser. No. 436,455, Nov. 14, 1989, Pat. No. 5,188,934.

[51] Int. Cl.$^6$ ............... C07D 311/82; C07D 311/94; C07D 311/78; C12Q 1/68
[52] U.S. Cl. ................. 435/6; 436/96; 436/98; 935/77; 935/98
[58] Field of Search ................ 435/6; 436/96, 436/98; 935/77, 98

[56] References Cited

U.S. PATENT DOCUMENTS

| | | | |
|---|---|---|---|
| 4,318,846 | 3/1982 | Khanna et al. | 260/112 |
| 4,439,356 | 3/1984 | Khanna et al. | 260/112 |
| 4,481,136 | 11/1984 | Khanna et al. | 260/112 |
| 4,647,578 | 3/1987 | Crounse et al. | 514/454 |
| 4,855,225 | 8/1989 | Fung et al. | 436/6 |
| 4,933,471 | 6/1990 | Lee | 549/33 |
| 4,997,928 | 3/1991 | Hobbs, Jr. | 536/27 |
| 5,066,580 | 11/1991 | Lee | 435/721 |
| 5,188,934 | 2/1993 | Menchen et al. | 435/6 |

FOREIGN PATENT DOCUMENTS

| | | |
|---|---|---|
| 0 050 684 | 5/1982 | European Pat. Off. . |
| 8500360 | 9/1985 | United Kingdom . |
| WO 91/07507 | 5/1991 | WIPO . |

OTHER PUBLICATIONS

* Connell et al., "Automated DNA Sequence Analysis," *BioTechniques*, 5(4) : 342–348 (1987).
* Karger et al., "Multiwavelength Fluorescence Detection for DNA Sequencing Using Capillary Electrophoresis," *Nucleic Acids Research*, 19(18) : 4955–4962 (1991).
* Wehry, chapter 3 in Guilbault, editor, Practical Fluorescence, 2nd .Ed., (Marcel Dekker, New York, 1990).
* Wehry, chapter 4 in Guilbault, editor, Practical Fluorescence, 2nd. Ed., (Marcel Dekker, New York, 1990).
* Haugland, chapter 2 in Steiner, editor, Excited States of Biopolymers (Plenum Press, New York, 1983).
Lee et al., "Vita Blue: A New 644–nm Excitable Fluorescent Dye for Cell Analysis," *Cytometry*, 10:151–164 (1989).
Pringle, et al., "Automated Nucleotide Sequence Analysis Accuracy Is Strongly Dependent Upon Optimal Template Levels and Avoidance of Gel Overload," *DNA Core Facilities Newsletter*, 1:15–21 (1988).
Kaambara, et al., "Optimization of Parameters in a DNA Sequenator Using Fluorescence Detection," *Biotechnology*, 6:816–821 (1988).
Smith, et al., "Fluorescence Detection in Automated DNA Sequence Analysis," *Nature*, 321:674–679 (1986).
Prober, et al., "A System for Rapid DNA Sequencing with Fluorescent Chain–Terminating Dideoxynucleotides," *Science*, 238:336–341 (1987).
Kirkbright, G.F., "Chapter 9—Fluorescent Indicators," from Indicators (Bishop, E., ed., Pergamon Press, Oxford et al., pp. 685–698).
Marshall, P.N., "Rules for the Visible Absorption Spectra of Halogenated Fluorescein Dyes," *Histochemical Journal*, 7:299–303 (1975).
Smith et al, "The Synthesis and Use of Fluorescent Oligonucleotides in DNA Sequence Analysis", *Methods in Enzymology*, 155: 260–301 (1987).

*Primary Examiner*—Frederick Krass
*Attorney, Agent, or Firm*—Stephen M. Macevicz; Vincent M. Powers

[57] ABSTRACT

Long wavelength, narrow emission bandwidth fluorecein dyes are provided for detecting spacially overlapping target substances. The dyes comprise 4,7-dichlorofluoresceins, and particularly 2',4',5',7'-tetrachloro-4,7-dichloro-5- (and 6-) carboxyfluoresceins. Methods and kits for using the dyes in DNA analysis are provided.

6 Claims, No Drawings

4, 7-DICHLOROFLUORESCEIN DYES AS MOLECULAR PROBES

This application is a continuation of application Ser. No. 08/400,780 filed Mar. 8, 1995, now U.S. Pat. No. 5,654,442 issued Aug. 5, 1997, which is a continuation of Ser. No. 07/939,813 filed Sep. 3, 1992, abandoned, which is a continuation-in-part of Ser. No. 07/436,455 filed Nov. 14, 1989, now U.S. Pat. No. 5,188,934, the disclosures of which are all incorporated herein by reference.

FIELD OF THE INVENTION

The invention relates generally to fluorescent labelling techniques, and more particularly, to the use of 4,7-dichlorofluoresceins for detecting multiple target substances in the same sample.

BACKGROUND

Many diagnostic and analytical techniques require that multiple target substances in the same sample be labelled with distinguishable fluorescent tags, e.g. Lanier et al, J. Immunol., Vol. 132, pgs. 151–156 (1984)(flow cytometry); Gray et al, Chromosoma, Vol. 73, pgs. 9–27 (1979)(flow system karyotyping); Fung et al, U.S. Pat. No. 4,855,225 (DNA sequencing); and Mayrand et al, Applied and Theoretical Electrophoresis, Vol. 3, pgs. 1–11 (1992)(analysis of electrophoretically separated polymerase chain reaction (PCR) products). This requirement is particularly difficult to satisfy in DNA sequence analysis where at least four spectrally resolvable dyes are needed in most automated sequencing approaches.

Presently, there are two basic approaches to DNA sequence determination: the dideoxy chain termination method, e.g. Sanger et al, Proc. Natl. Acad. Sci., Vol. 74, pgs. 5463–5467 (1977); and the chemical degradation method, e.g. Maxam et al, Proc. Natl. Acad. Sci., Vol. 74, pgs. 560–564 (1977). The chain termination method has been improved in several ways, and serves as the basis for all currently available automated DNA sequencing machines, e.g. Sanger et al, J. Mol. Biol., Vol. 143, pgs. 161–178 (1980); Schreier et al, J. Mol. Biol., Vol. 129, pgs. 169–172 (1979); Smith et al, Nucleic Acids Research, Vol. 13, pgs. 2399–2412 (1985); 35Smith et al, Nature, Vol. 321, pgs. 674–679 (1987); Prober et al, Science, Vol. 238, pgs. 336–341 (1987), Section II, Meth. Enzymol., Vol. 155, pgs. 51–334 (1987); Church et al, Science, Vol 240, pgs. 185–188 (1988); and Connell et al, Biotechniques, Vol. 5, pgs. 342–348 (1987).

Both the chain termination and chemical degradation methods require the generation of one or more sets of labeled DNA fragments, each having a common origin and each terminating with a known base. The set or sets of fragments must then be separated by size to obtain sequence information. In both methods, the DNA fragments are separated by high resolution gel electrophoresis. In most automated DNA sequencing machines, fragments having different terminating bases are labeled with different fluorescent dyes, which are attached either to a primer, e.g. Smith et al (1987, cited above), or to the base of a terminal dideoxynucleotide, e.g. Prober et al (cited above). The labeled fragments are combined and loaded onto the same gel column for electrophoretic separation. Base sequence is determined by analyzing the fluorescent signals emitted by the fragments as they pass a stationary detector during the separation process.

Obtaining a set of dyes to label the different fragments is a major difficulty in such DNA sequencing systems. First, it is difficult to find three or more dyes that do not have significantly overlapping emission bands, since the typical emission band halfwidth for organic fluorescent dyes is about 40–80 nanometers (nm) and the width of the visible spectrum is only about 350–400 nm. Second, even when dyes with non-overlapping emission bands are found, the set may still be unsuitable for DNA sequencing if the respective fluorescent efficiencies are too low. For example, Pringle et al, DNA Core Facilities Newsletter, Vol. 1, pgs. 15–21 (1988), present data indicating that increased gel loading cannot compensate low fluorescent efficiencies. Third, when several fluorescent dyes are used concurrently, excitation becomes difficult because the absorption bands of the dyes are often widely separated. The most efficient excitation occurs when each dye is illuminated at the wavelength corresponding to its absorption band maximum. When several dyes are used one is often forced to make a trade off between the sensitivity of the detection system and the increased cost of providing separate excitation sources for each dye. Fourth, when the number of differently sized fragments in a single column of a gel is greater than a few hundred, the physiochemical properties of the dyes and the means by which they are linked to the fragments become critically important. The charge, molecular weight, and conformation of the dyes and linkers must not adversely affect the electrophoretic mobilities of closely sized fragments so that extensive band broadening occurs or so that band positions on the gel become reversed, thereby destroying the correspondence between the order of bands and the order of the bases in the nucleic acid whose sequence is to be determined. Finally, the fluorescent dyes must be compatible with the chemistry used to create or manipulate the fragments. For example, in the chain termination method, the dyes used to label primers and/or the dideoxy chain terminators must not interfer with the activity of the polymerase or reverse transcriptase employed.

Because of these severe constraints only a few sets of fluorescent dyes have been found that can be used in automated DNA sequencing and in other diagnostic and analytical techniques, e.g. Smith et al (1985, cited above); Prober et al (cited above); Hood et al, European patent application 8500960; and Connell et al (cited above).

In view of the above, many analytical and diagnostic techniques, such as DNA sequencing, would be significantly advanced by the availability of new fluorescent dyes (1) which are physiochemically similar to readily available dyes, (2) which permit detection of spacially overlapping target substances, such as closely spaced bands of DNA on a gel, (3) which extend the number of bases that can be determined on a single gel column by current methods of automated DNA sequencing, and (4) which are amenable for use with a wide range of preparative and manipulative techniques.

SUMMARY OF THE INVENTION

The invention is directed to a method of concurrently detecting spacially overlapping target substances using 4,7-dichlorofluorescein dyes, and in particular, methods of DNA sequence determination employing 4,7-dichlorofluorescein dyes. The invention also includes 2',7'-dichloro-5 (and 6-)carboxy-4,7,-dichlorofluorescein defined by Formula I.

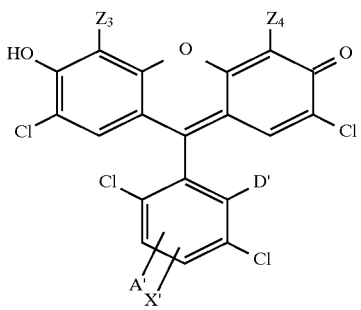

Formula I wherein:
- A' is hydrogen, fluoro, chloro, a linking functionality, such as isothiocyanate, succinimidyl carboxylate, or phosphoramidite, or a group, such as carboxyl, sulfonyl, or amino, that may be converted to a linking functionality; preferably A' is a linking functionality or a group that may be converted to a linking functionality;
- X' is hydrogen, fluoro or chloro, such that whenever A' is a substituent of the 6 carbon atom X' is a substituent of the 5 carbon atom, and whenever A' is a substituent of the 5 carbon atom X' is a substituent of the 6 carbon atom; preferably, X' is hydrogen;
- $Z_3$ is hydrogen, fluoro, chloro, a linking functionality, such as isothiocyanate, succinimidyl carboxylate, or phosphoramidite, or a group, such as carboxyl, sulfonyl, or methylamino, that that may be converted to a linking functionality; preferably, $Z_3$ is hydrogen or chloro;
- $Z_4$ is hydrogen, fluoro, chloro, a linking functionality, such as isothiocyanate, succinimidyl carboxylate, or phosphoramidite, or a group, such as carboxyl, sulfonyl, or methylamino, that may be converted to a linking functionality; preferably, $Z_4$ is hydrogen or chloro;
- D' is fluoro, chloro, or an acidic anionic group; preferably, D' is carboxyl or sulfonyl, and most preferably D' is carboxyl;
- and wherein at least one of A', $Z_3$, and $Z_4$ is a linking functionality or a group that may be converted to a linking functionality. Preferably, only one of A', $Z_3$, and $Z_4$ is a linking functionality or a group that may be converted to a linking functionality.

The invention also includes kits for carrying out the method of the invention. Generally, kits are provided for detecting a plurality of electrophoretically separated classes of DNA fragments. In particular, kits are included for carrying out DNA sequencing wherein at least one class of primer extension product is fluorescently labelled with a 4,7-dichlorofluorescein dye. Such DNA sequencing kits include kits with dye-labelled primers and, as an alternative embodiment, kits with dye-labelled terminators.

Throughout, the *Colour Index* (Association of Textile Chemists, 2nd Ed., 1971) carbon numbering scheme is used, i.e. primed numbers refer to carbons in the xanthene structure and unprimed numbers refer to carbons in the 9'-phenyl.

The invention is based in part on the discovery that the fluorescent properties of 4,7-chloro-5- (and 6-)carboxyfluorescein and related dyes are highly favorable for use as molecular probes. Their emission band widths are generally 20–30 percent narrower than analogs lacking the 4,7-dichloro derivatives, their emission and absorption maxima are at wavelengths generally about 10–30 nm higher than analogs lacking the 4,7-dichloro derivatives, and their fluorescent efficiencies are high, in some cases being nearly triple those of analogs lacking the 4,7-dichloro derivatives.

DETAILED DESCRIPTION OF THE INVENTION

As mentioned above, the invention is based in part on the discovery of a class of fluorescein dyes that have absoption and emission maxima at unusually long wavelengths, narrow emission band widths and other favorable fluorescent properties. In addition, the invention includes the novel fluorescein analogs defined by Formula I as members of this class of dyes. These dyes permit the assembly of novel sets of spectrally resolvable, physiochemically similar dyes particularly useful in automated DNA sequence analysis.

As used herein the term "spectrally resolvable" in reference to a set of dyes means that the fluorescent emission bands of the dyes are sufficiently distinct, i.e. sufficiently non-overlapping, that target substances to which the respective dyes are attached, e.g. polynucleotides, can be distinguished on the basis of the fluorescent signal generated by the respective dyes by standard photodetection systems, e.g. employing a system of band pass filters and photomultiplier tubes, or the like, as exemplified by the systems described in U.S. Pat. Nos. 4,230,558, 4,811,218, or the like, or in Wheeless et al, pgs. 21–76, in *Flow Cytometry: Instrumentation and Data Analysis* (Academic Press, New York, 1985).

The term "lower alkyl" as used herein directly or in connection with ethers denotes straight-chain and/or branched chain alkyl groups containing from 1–6 carbon atoms, e.g. the term includes methyl, ethyl, propyl, isopropyl, tert-butyl, isobutyl, and the like. More preferably, the term "lower alkyl" denotes an alkyl having from 1 to 3 carbon atoms.

The term "halo" as used herein denotes the halogen atoms fluorine, chlorine, bromine, and iodine; more preferably, the term denotes fluorine or chlorine; and most preferably, the term denotes chlorine.

Preferably, the 4,7-dichloro-5- (and 6-) carboxyfluorescein dyes of the invention include those defined by Formula II.

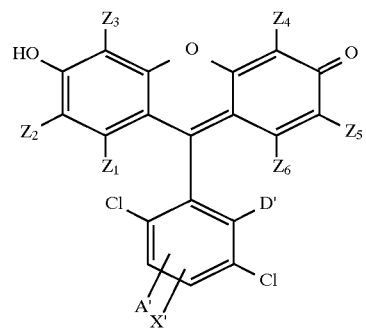

Formula II wherein:
- A', D' and X' are defined as above;
- $Z_1$ is hydrogen or, when taken with $Z_2$, benzo;
- $Z_2$, when taken alone, is hydrogen, halo, lower alkyl, lower alkyloxy, or a group, such as carboxyl, sulfonyl, or methylamino, that may be converted to an active linking functionality, or when taken with $Z_1$, $Z_2$ is methylamino, that may be converted to an active linking functionality, or when taken with $Z_5$, $Z_6$ is benzo;

preferably, when taken alone, $Z_6$ is hydrogen, methyl, ethyl, fluoro, chloro, methoxy, or ethoxy;

and wherein at least one of A', $Z_2$, $Z_3$, $Z_4$, and $Z_5$ is a group that may be converted to an linking functionality. Preferably, only one of A', $Z_2$, $Z_3$, $Z_4$, and $Z_5$ is a group that may be converted to an active linking functionality.

Many dyes for use in the invention are commercially available or can be synthesized by techniques known in the art, e.g. Ghatak et al, J. Ind. Chem. Soc., Vol. 6, pgs. 465–471 (1929); and Khanna et al, U.S. Pat. No. 4,439,356. Alternatively, fluorescein analogs, i.e. A'=D'=carboxyl, can be synthesized by reacting substituted resorcinol with substituted benzophenone or with substituted trimellitic acid in the presence of propionic acid, as illustrated in the examples. Sulfonylfluoresceins, i.e. A' or D' is sulfonyl, are synthesized following the methods disclosed by Lee et al, Cytometry, Vol. 10, pgs. 151–164 (1989), modified by substituting appropriate reactants to give 5- or 6-carboxyl- or sulfonylfluorescein products. Preferably, when labeling polynucleotides in DNA sequencing the 5- and 6- isomers of the dyes are used separately because they typically have slightly different electrophoretic mobilities that can lead to band broadening if mixtures of the isomers are used. The 5- and 6- isomers of the dyes are readily separated by reverse phase HPLC, e.g. Edmundson et al, Mol. Immunol., Vol. 21, pg. 561 (1984). Generally, it is believed that the first eluting peak is the 6- isomer and the second eluting peak is the 5- isomer.

Dyes of the invention can be attached to target substances by a variety of means well known in the art. For example, Haugland, *Handbook of Fluorescent Probes and Research Chemicals* (Molecular Probes, Inc., Eugene, 1989) provides guidance and examples of means for linking dyes to target substances. Substituent A is converted to a linking functionality that can be reacted with a complementary functionality on a target substance to form a linking group. The following table lists illustrative linking functionalities that can be formed whenever A is carboxyl, sulfonyl or amine, suitable complementary functionalities, and the resulting linking groups suitable for use with the invention.

| Linking Functionality | Complementary Functionality | Linking Group |
|---|---|---|
| —NCS | —NH₂ | —NHCSNH— |
| —NH-(dichlorotriazinyl) | —NH₂ | —NH-(chlorotriazinyl)-NH— |
| —SO₂X | —NH₂ | —SO₂NH— |
| —C(O)—O—N(succinimidyl) | —NH₂ | —C(O)—NH— |
| —NH—C(O)—CH₂I | —SH | —NH—C(O)—CH₂—S— |
| —N(maleimidyl) | —SH | —N(succinimidyl-S)— |
| —O—P(R₁N R₂)(O—R₃) | —OH | —O—P(=O)(O—R₃)—O— |

Preferably the linking functionality is isothiocyanate, sulfonyl chloride, 4,6-dichlorotriazinylamine, or succinimidyl carboxylate whenever the complementary functionality is amine. And preferably the linking functionality is maleimide, or iodoacetamide whenever the complementary functionality is sulfhydryl. Succinimidyl carboxylates can be formed by condensing the 5- and/or 6-carboxyls of the above dyes with N-hydroxysuccinimide using dicyclohexylcarbodiimide (DCC), e.g. as illustrated in examples 6 and 8 of Khanna et al, U.S. Pat. No. 4,318,846, and Kasai et al, *Anal. Chem.*, Vol. 47, pgs. 34–37 (1975). Accordingly, these references are incorporated by reference. Dye phosphoramidites are formed as taught by Stein et al, Gene, Vol. 72, pgs. 333–341 (1988); Fung et al, U.S. Pat. No. 4,757,141; European patent application 89116946.8 filed 13 Sep. 1989; and European patent application 88307934.5 filed 26 Aug. 1988. Substituents $R_1$, $R_2$, and $R_3$ can take a variety of forms, e.g. as taught by Beaucage et al, Tetrahedron, Vol. 48, pgs. 2223–2311 (1992); Caruthers, pgs. 47–94 in Narang, editor, Synthesis and Applications of DNA and RNA (Academic Press, New York, 1987); and the like. Preferably, $R_1$ and $R_2$, taken separately, are methyl, ethyl, or isopropyl, and $R_1$ and $R_2$, taken together with the nitrogen to which they are attached, is a heterocycle having from four to eight carbon atoms and one to two heteroatoms selected from the group consisting of nitrogen, oxygen, and sulfur. More preferably, $R_1$ and $R_2$, taken together with the nitrogen to which they are attached is morpholino. Preferably, $R_3$ is selected from the group consisting of methyl, chlorophenyl, β-cyanoethyl, methylsulfonylethyl, and nitrophenylethyl. Preferably, the phosphoramidite-derived linking group is oxidized to form a phosphorus(V) linkage, e.g. as taught by Beaucage et al (cited above); Stec et al, PCT application PCT/US91/01010; Beaucage et al, U.S. Pat. No. 5,003,097; or the like.

When dyes of the invention are used to label dideoxynucleotides for DNA sequencing, preferably they are linked to the 5 carbon of pyrimidine bases and to the 7 carbon of 7-deazapurine bases. For example, several suitable base labeling procedures have been reported that can be used with the invention, e.g. Gibson et al, Nucleic Acids Research, Vol. 15, pgs. 6455–6467 (1987); Gebeyehu et al, Nucleic Acids Research, Vol. 15, pgs. 4513–4535 (1987); Haralambidis et al, Nucleic Acids Research, Vol. 15, pgs. 4856–4876 (1987); and the like. Preferably, the linking group between the dye and a base is formed by reacting an N-hydroxysuccinimide (NHS) ester of a dye of the invention with an alkynylamino-derivatized base of a dideoxynucleotide. Preferably, the linking group is 3-carboxyamino-1-propynyl. The synthesis of such alkynylamino-derivatized dideoxynucleotides is taught by Hobbs et al in European patent application number 87305844.0 and U.S. Pat. No. 5,047,519, which are incorporated herein by reference. Briefly, the alkynylamino-derivatized dideoxynucleotides are formed by placing the appropriate halodideoxynucleoside (usually 5-iodopyrimidine and 7-iodo-7-deazapurine dideoxynucleosides as taught by Hobbs et al (cited above)) and Cu(I) in a flask, flushing with Ar to remove air, adding dry DMF, followed by addition of an alkynylamine, triethylamine and Pd(O). The reaction mixture can be stirred for several hours, or until thin layer chromatography indicates consumption of the halodideoxynucleoside. When an unprotected alkynylamine is used, the alkynylamino-nucleoside can be isolated by concetrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

Target substances of the invention can be virtually anything that the dyes of the invention can be attached to. Preferably the dyes are covalently attached to the target substances. Target substances include proteins, polypeptides, peptides, polysaccharides, polynucleotides, lipids, and combinations and assemblages thereof, such as chromosomes, nuclei, living cells, such as bacteria, other microorganisms, and mammalian cells, tissues, and the like. As used herein the term "polynucleotide" means a single stranded or double stranded chain of DNA or RNA in the size range of a few bases in length to several thousand bases in length, e.g. from 6 to a few tens to several hundreds or to several thousands of bases in length (if single stranded), or in the size range of a few basepairs in length to several thousand basepairs in length, e.g. from 6 to a few tens to several hundred or to several thousand basepairs in length (if double stranded).

A number of complementary functionalities can be attached to the 5' or 3' ends of synthetic oligonucleotides and polynucleotides, e.g. amino groups, Fung et al, U.S. Pat. No. 4,757,141 and Miyoshi et al, U.S. Pat. No. 4,605,735; or sulfhydryl groups, Connolly, *Nucleic Acids Research*, Vol. 13, pgs. 4485–4502 (1985), and Spoat et al, *Nucleic Acids Research*, Vol. 15, pgs. 4837–4848 (1987).

Dyes of the invention are particularly well suited for identifying classes of polynucleotides that have been subjected to a biochemical separation procedure, such as gel electrophoresis, where a series of bands or spots of target substances having similar physiochemical properties, e.g. size, conformation, charge, hydrophobicity, or the like, are present in a linear or planar arrangement. As used herein, the term "bands" includes any spacial grouping or aggregation of target substance on the basis of similar or identical physiochemical properties. Usually bands arise in the separation of dye-polynucleotide conjugates by electrophoresis, particularly gel electrophoresis.

Classes of polynucleotides can arise in a variety of contexts. For example, they can arise as products of restriction enzyme digests, or as extension products in polymerase or ligase reactions. Preferably, classes identified in accordance with the invention are defined in terms of terminal nucleotides so that a correspondence is established between the four possible terminal bases and the members of a set of spectrally resolvable dyes. Such sets are readily assembled from the dyes of the invention by measuring emission and absorption bandwidths with commercially available spectrophotometers. More preferably, the classes arise in the context of the chemical or chain termination methods of DNA sequencing, and most preferably the classes arise in the context of the chain termination method. In either method dye-polynucleotide conjugates are separated by standard gel electrophoretic procedures, e.g. Gould and Matthews, cited above; Rickwood and Hames, Eds., *Gel Electrophoresis of Nucleic Acids: A Practical Approach*, (IRL Press Limited, London, 1981); or Osterman, *Methods of Protein and Nucleic Acid Research*, Vol. 1 (Springer-Verlag, Berlin, 1984). Preferably the type of gel is polyacrylamide having a concentration (weight to volume) of between about 2–20 percent. More preferably, the polyacrylamide gel concentration is between about 4–8 percent. Preferably the gel includes a strand separating, or denaturing, agent. Detailed procedures for constructing such gels are given by Maniatis et al., "Fractionation of Low Molecular Weight DNA and RNA in Polyacrylamide Gels Containing 98% Formamide or 7M Urea," in *Methods in Enzymology*, Vol. 65, pgs. 299–305 (1980); Maniatis et al., "Chain Length Determination of Small Double- and Single-Stranded DNA Molecules by Polyacrylamide Gel Electrophoresis," *Biochemistry*, Vol. 14, pgs. 3787–3794, (1975); and Maniatis et al., *Molecular Cloning: A Laboratory Manual* (Cold Spring Harbor Laboratory, New York, 1982), pgs. 179–185. Accordingly these references are incorporated by reference. The optimal gel concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations. By way of example, polynucleotides having sizes in the range of between about 20–300 bases have been separated and detected in accordance with the invention in the following gel: 6 percent polyacrylamide made from 19 parts to 1 part acrylamide to bis-acrylamide, formed in a Tris-borate EDTA buffer at pH 8.3 (measured at 250° C.) with 48 percent (weight/volume) urea. The gel was run at 50° C.

The dye-polynucleotide conjugates on the gel are illuminated by standard means, e.g. high intensity mercury vapor lamps, lasers, or the like. Preferably, the dye-polynucleotides on the gel are illuminated by laser light generated by a argon ion laser, particularly the 488 and 514 nm emission lines of an argon ion laser. Several argon ion lasers are available commercially which lase simultaneously at these lines, e.g. Cyonics, Ltd. (Sunnyvale, Calif.) Model 2001, or the like.

In the chain termination method, dyes of the invention can be attached to either primers or dideoxynucleotides. Dyes can be linked to a complementary functionality on the 5' end of the primer, e.g following the teaching in Fung et al, U.S. Pat. No. 4,757,141 which is incorporated herein by reference; on the base of a primer, e.g. following the teachings of Ward et al, U.S. Pat. No. 4,711,955; directly to the 5'-hydroxyl via a phosphoramidite linking functionality; or on the base of a dideoxynucleotide, e.g. via the alkynylamino linking groups disclosed by Hobbs et al, European patent application number 87305844.0 which is incorporated herein by reference.

Kits of the invention can take a variety of forms, but usually provide the means for the fluoresecent detection of multiple DNAs separated by size. Kits may be used for detecting amplified nucleic acids separated by size (e.g. by electrophoresis), for DNA sequencing, and the like. Generally, the kits will include either an oligonucleotide labelled with a 4,7-dichlorofluorescein dye, or in an embodiment of the DNA sequencing kit a dye-terminator mix wherein at least one of the dye-terminators is labelled with a 4,7-dichlorofluorecein dye. Usually, the dye-terminator is a dideoxynucleoside triphosphate, as described above, labelled with a fluorescent dye.

Kits for detecting amplified nucleic acids comprise at least one oligonucleotide labelled with a 4,7-dichlorofluorescein dye, an enzyme selected from the group consisting of nucleic acid polymerase and nucleic acid ligase, and a reaction buffer. Whenever the kit includes a DNA polymerase, it further includes a nucleoside triphosphate mix, e.g. a 50 mM aqueous solution of EDTA containing the appropriate concentration of nucleoside triphosphates for a particular application, e.g. amplification, sequencing, or the like. When the kit provides a nucleoside triphosphate mix for DNA sequencing it is understood that such triphosphates include analogs, such as nucleoside-5'-O-(1-thiotriphosphates), e.g. as taught by Lee et al, Nucleic Acids Research, Vol. 20, pgs. 2471–2483 (1992). Nucleic acid polymerases include DNA polymerases, RNA polymerases, and reverse transcriptases, and the like. Preferably, whenever the kit is for PCR amplification, the nucleic acid polymerase is Taq polymerase, e.g. as disclosed by Gelfand, U.S. Pat. No. 4,889,818. Guidance for selecting a PCR reaction buffers and nucleoside triphosphate mixes for particular embodiments can be found in Innis et al, Editors, PCR Protocols: A Guide to Methods and Applications (Academic Press, New York, 1990). A typical 10X PCR reaction buffer comprises 15 mM $MgCl_2$, 500 mM KCl, and Tris-HCl, pH 8.3.

Preferably, whenever the kit permits a ligase-based amplification reaction, e.g. as disclosed by Landegren et al, U.S. Pat. No. 4,988,617 or the like, the nucleic acid ligase is a thermostable ligase, such as disclosed by Barany, Proc. Natl. Acad. Sci., Vol. 88, pgs. 189–193 (1991). Guidance for selecting a ligase-based reaction buffer can be found in Landegren et al (cited above), Wu et al, Genomics, Vol. 4, pgs. 560–569 (1989); Barany (cited above), and Nickerson et al, Proc. Natl. Acad. Sci., Vol. 87, pgs. 8923–8927 (1990). A typical ligation reaction buffer comprises 20 mM Tris-HCl, pH 7.6; 50 mM KCl; 10 mM $MgCl_2$; 1 mM EDTA; 10 mM $NAD^+$, and 10 mM dithiothreitol.

The dye-labelled oligonucleotides of the kit can have a wide range of lengths, but preferably their length are in the range of 6 to 60 nucleotides. More preferably, the oligonucleotides for ligation kits are in the range of 6 to 30 nucleotides in length, and most preferably, the oligonucleotides for ligation kits are in the range of 16 to 25 nucleotides in length. The particular nucleotide sequence of the oligonucleotides are, of course, dictated by the target sequences sought to be amplified. In embodiments for PCR amplification, selection of oligonucleotides for use as PCR primers is well known in the art, e.g. Innis et al (cited above), Hillier and Green, PCR Methods and Applications, Vol. 1, pgs. 124–128 (1991), and the like.

Preferably, in kits for DNA sequencing wherein dye-terminators are provided, each dideoxynucleoside triphosphate is separately labelled with a dye selected from the set comprising 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6 -carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8'-dibenzo-4',5'-dichloro-5- and 6-carboxy-4,7-dichlorofluorescein, 2',7'-dichloro-5 and 6-carboxy-4,7-dichlorofluorescein, and 2',4',5',7'-tetrachloro-5 and 6-carboxy-4,7-dichlorofluorescein. More preferably, dideoxythymidine triphosphate is labelled with 6-carboxyfluorescein ("6-FAM"), dideoxycytidine triphosphate is labelled with 2',4',5',7'-tetrachloro-5-carboxyfluorescein ("5-ZOE"), dideoxyadenosine triphosphate is labelled with 2',4',5',7'-tetrachloro-4,7-dichloro-5-carboxyfluorescein ("5-HEX"), and dideoxyguanosine triphosphate is labelled with 1',2',7',8'-dibenzo-4,7-dichloro-5-carboxyfluorescein ("5-NAN"). It is understood that dideoxyadenosine includes 2'3'-dideoxy-7-deazaadenosine and dideoxyguanosine includes 2',3'-dideoxy-7-deazaguanosine and 2',3'-dideoxy-7-deazainosine, and dideoxythymidine includes 2',3'-dideoxyuridine. Usually, the dideoxynucleoside triphosphates are labelled by way of a linking group. Preferably, the linking group links a 5 carbon of the 2',3'-dideoxycytidine or 2',3'-dideoxyuridine to a 5 or 6 carbon of a dye, and the linking group links a 7 carbon of the 2',3'-dideoxy-7-deazaadenosine or 2',3'-dideoxy-7-guanosine or 2',3'-dideoxy-7-deazainosine to a 5 or 6 carbon of a dye. Preferably, the linking group is carboxyaminoalkynyl, and most preferably, the linking group is 3-carboxyamino-1-propynyl.

Preferably, in kits for DNA sequencing wherein dye-terminators are provided, the nucleic acid polymerase is Sequenase™.

EXAMPLE 1

4,7-dichloro-5-(and 6-)carboxyfluorescein ("ALF")

0.58 g of 3,6-dichlorotrimellitic acid, 0.72 g of resorcinol, 0.5 ml concentrated sulfuric acid, and 3 ml of propionic acid were refluxed 12 hours under argon. The reaction mixture was poured into 150 ml water; the precipitate was dried, taken into 3 ml pyridine and acetylated with 2 ml acetic anhydride for 1 hour. The acetylation mixture was taken into 100 ml ethyl acetate, washed with 1N hydrochloric acid, water, and evaporated to dryness. The residue was placed on 15 grams of silica gel and eluted with 50 ml ethyl acetate, then 4:1 ethyl acetate:methanol. Fractions containing UV active material with $R_f$ of about 0.2 (4:1 ethyl acetate:methanol/silica gel) were evaporated to dryness. This residue was dissolved in 10 ml methanol and then 1 ml of 4N sodium hydroxide was added. After 10 minutes, the reaction mixture was diluted to 200 ml with water and then 0.5 ml of concentrated hydrochloric acid was added. The total mixture was extracted with 200 ml of ethyl acetate, after which the ethyl acetate was dried with sodium sulfate and evaporated to dryness yielding 102 mg of yellow-green solid.

EXAMPLE 2

4,7-dichloro-5-(and 6-) carboxyfluorescein N-hydroxysuccinimide (NHS) Ester 13.7 mg of fluorescein from Example I, 3,3 mg of 30NHS, 6,4 mg DCC, and 1 ml ethyl acetate were stirred 0.5 hours. The solid was filtered, and the supernatant was washed three times with 1:1 brine:water, dried with sodium sulfate, and evaporated to dryness yielding 15 mg of NHS ester.

EXAMPLE 3

Conjugation of 4,7-dichloro-5-(and 6-)carboxyfluorescein with aminoalkyloligonucleotides 5 mg of NHS ester from Example II were dissolved 5 in 20 ul of DMSO; 3 ul of this solution were added to a solution consisting of 20 ul of 1.0 mM 5'-aminohexylphosphate oligonucleotide (an 18-mer) in water and 10 ul of 1M sodium bicarbonate/sodium carbonate buffer, pH 9.0. After one hour in the dark, the solution was passed through a 10 ml Sephadex G-25 (medium) column with 0.1M triethylammonium acetate buffer, pH 7.0. The band of colored material eluting in the exclusion volume was collected. Reverse phase HPLC showed two major fluorescent peaks, corresponding to the 5- and 6- isomers of the dye conjugated onto the DNA. The peaks were collected, and the fluorescence spectra in 50% urea at pH 8.0 showed full width at half max of 34 nm with the emission maxima at 528 nm.

EXAMPLE 4

2',7'-dimethoxy-5-(and 6-)carboxy 4,7-dichlorofluorescein ("BUB")

The procedure of Example I was followed except that the following materials and quantities were substituted: 1,47 g 4-methoxyresorcinol, 0.60 g of 3,6-dichlorotrimellitic acid, 0.2 ml concentrated sulfuric acid, and 4 ml propionic acid. The procedure yielded 0.180 g of 4,7-dichloro-2',7'-dimethoxy-5-(and 6-)carboxyfluorescein.

EXAMPLE 5

2',7'-dimethoxy-5-(and 6-)carboxy 4,7-dichlorofluorescein NHS Ester 18 mg of this dye NHS ester were prepared as in Example II using 18 mg of dye from Example IV, 3.5 mg NHS, 6.4 mg DCC, and 2 ml ethyl acetate.

EXAMPLE 6

Conjugation of 4,7-dichloro-2',7'-dimethoxy 5-(and 6-)carboxyfluorescein with Aminoalkyloligonucleotide The procedure of Example III was followed using the dye NHS ester of Example V. The fluorescence spectra of the two peaks collected during reverse phase HPLC showed full widths at half max of 37 nm with emission maxima at 544 nm in 50% urea at pH 8.2.

EXAMPLE 7

2',7'-dimethoxy-4',5'-dichloro-5-(and 6-)carboxy-4,7-dichlorofluorescein ("LOU")

This dye was prepared from the dye of Example IV and sodium hypochlorite in aqueous sodium hydroxide.

EXAMPLE 8

4,7-dichloro-2',7'-dimethoxy-4',5'-dichloro-5-(and 6-) carboxyfluorescein NHS Ester 1.1 mg of this dye NHS ester was prepared from 0.7 mg of the dye from Example VII, 0.45 mg of NHS, 0.7 mg DCC, and 0.2 ml ethyl acetate as in Example II.

EXAMPLE 9

Conjugation of 4,7-dichloro-2',7'-dimethoxy 4',5'-dichloro-5-(and 6-)carboxyfluorescein with Aminoalkyloligonucleotides The dye oligonucleotide conjugate of this example was prepared as in Example III using the dye NHS ester from Example VIII. The fluorescence spectra of the two peaks collected during reverse phase HPLC showed full widths at half max of 38 nm with emission maxima at 558 nm in 50% urea at pH 8.2.

EXAMPLE 10

1',2',7',8'-dibenzo-5-(and 6-)carboxy-4,7-dichlorofluorescein ("NAN")

First, 3,6-dichlorotrimellitic add trichloride was prepared: A mixture of 0.5 g of 3,6-dichlorotrimellitic acid and 1.3 g of phosphorous pentachloride was heated at 130° C. for 40 minutes. The mixture was cooled to room temperature and poured into ice. The mixture was then extracted with 40 ml ether, the organic fraction was washed twice with 15 ml water, dried with $MgSO_4$, and concentrated to a clear oil (0.7 g). The acid trichloride was used without further purification. NAN was prepared as follows: A mixture of 2.7 g of 1,3-dihydroxynaphthalene, 2.84 g of 3,6-dichlorotrimellitic acid trichloride, and 8 ml of propionic acid was refluxed for 2 hours. Water (50 ml) and ethyl acetate (50 ml) were added. The layers were separated and the organic layer was extracted three times with 50 ml of 1M $NaHCO_3$. The aqueous solution was heated to boiling and acidified with concentrated HCl. The resulting red solid (0.2 g) was filtered and dried.

EXAMPLE 11

1',2',7',8'-dibenzo-4',5'-dichloro-5-(and 6-)carboxy 4, 7-dichlorofluorescein ("DEB")

20 mg of NAN, sodium hydroxide (34 ul of a 15% solution), water (1 ml, and sodium hypochlorite (170 ul of a 5% solution) were combined. Reverse phase HPLC showed 92% reaction. The solution was acidified with HCl, extracted with 20 ml of ethyl acetate, dried ($Na_2SO_4$), and concentrated to 20 mg. The solid was purified by chromatography on a silica gel column (1" diameter×2" height), eluting with 600:60:16 methylene chloride:methanol:acetic acid. The dye solution was concentrated, and dilute HCl and ethyl acetate added. The organic phase was dried ($MgSO_4$) and concentrated to 20 mg of DEB.

EXAMPLE 12

Formation of 1',2',7',8'-dibenzo-5-(and 6-)carboxy-4,7-dichlorofluorescein NHS Ester NAN (10 mg) was dissolved in 2 ml of ethyl acetate, and NHS (10 mg) and DCC (5 mg) was added. After 20 minutes, the solution was dark red in color and a crystalline solid appeared. Thin layer 5chromatography on a silica gel using 600:60:16 methylene chloride:methanol:acetic acid showed complete conversion to the NHS ester. The ethyl acetate solution was washed with dilute HCl, dried ($NaSO_4$) and concentrated to a red solid (15 mg).

EXAMPLE 13

Using ALF-, BUB-, LOU-, and NAN- oligonucleotide Conjugates as Dye-labeled Primers in DNA Sequence Analysis An all-fluorescein set of dyes was used to label DNA fragments in the chain termination approach employing the Applied Biosystems (Foster City, Calif.) Model 370A automated DNA sequencer. The manufacturer's protocol (User Bulletin DNA Sequencer Model 370, Issue No. 2, Aug. 12, 1987), which is incorporated by reference) was followed for amplification of the unknown DNA in M13 and preparation of separately labeled DNA fragments for gel electrophoretic separation. Dye-labeled primers were prepared as described in the examples above. That is, NHS esters of the respective dyes were prepared and reacted with the 5'-aminohexyl-derivatized M13 universal primer (5'-TCCCAGTCACGACGTTGT-3') to form the dye-labeled primers for the four separate dideoxy reaction mixtures. The following modifications were made to the standard protocol: 5-carboxy-4,7-dichlorofluorescein labeled the primer in the dideoxycytidine reaction, 2',7'-dimethoxy-5-carboxy-4,7-dichlorofluorescein labeled the primer in the dideoxyadenosine reaction, 2',7'-dimethoxy-4',5'-dichloro-5-carboxy-4,7-dichlorofluorescein labeled the primer in the dideoxyguanosine reaction, 1',2',7',8'-dibenzo-5-carboxy-4,7-dichlorofluorescein labeled the primer in the dideoxythymidine reaction, labeled DNA fragments from the respective reactions were combined in the following molar ratios for loading onto the gel: 1:1:4:2 ddC reaction:ddA reaction:ddG reaction:ddT reaction, and detection was accomplished with a modified filter wheel using 10 nm bandpass filters centered at 535, 550, 565, and 580 nm.

EXAMPLE 14

Using ALF-, BUB-, DEB-, and NAN-oligonucleotide Conjugates as Dye-labeled Primers in DNA Sequence Analysis The same procedure was followed as described for Example XIII, except for the following: (i) 1',2',7',8'-dibenzo-4',5'-dichloro-5-carboxy-4,7-dichlorofluorescein labeled the primer in the dideoxyguanosine reaction, (ii) labeled DNA fragments from the respective reactions were combined in the following molar ratios for loading on the gel: 1:1:2:15 ddC reaction:ddA reaction:ddG reaction:ddT reaction, and (iii) 5 nm bandpass filters were centered at 540, 560, 580, and 610 nm.

EXAMPLE 15

2',7'-dichloro-5(and 6)-carboxy-4,7-dichlorofluorescein ("5-(and 6-)TET")

A mixture of 4-chlororesorcinol (10 g), 4,7-dichlorotrimellitic acid (10 g), and methanesulfonic acid (30 mL) were combined and heated to 140° C.–150° C. for two hours. The red mixture was poured into water (100 mL) and extracted with ethyl acetate (100 mL). The organic phase was washed twice with dilute aqueous HCl and concentrated to a gold-brown solid (19 g). Pyridine (40 mL) and acetic anhydride (10 mL) were added to the solid and the mixture refluxed for 0.5 hours. The solution was allowed to cool for 1 hour at 4° C.

Crystals were separated by filtration to yield a white solid (5.4 g). Hydrolysis of a small portion (by addition of 0.02 mL of 0.1N NaCl and 0.02 mL of ethanol to 2 mg solid) followed by analysis on reverse phase HPLC showed that the solid contained a 92:8 ratio of isomers (6-carboxyTET:5-carboxyTET). A second recrystallization provided nearly isomerically pure dye as the diacetate (99:1 ratio). 5-TET can be recovered from the filtrate by hydrolysis of the diacetate form of 5-TET followed by recrystallization from acetonitrile.

Sodium hydroxide (3 g) and water (10 mL) were added to 6-TET diacetate (8.6 g)(obtained as the first of two peaks off the HPLC column). Additional water (50 mL) was added until the solution became homogeneous. To the dark red solution was added concentrated HCl (15 mL). A yellow precipitate formed. The mixture was extracted with ethyl acetate (100 mL). The organic layer was concentrated to a pale yellow, nearly colorless solid (7.4 g of 6-TET).

EXAMPLE 16

2',4',5',7'-tetrachloro-5-(and 6-)carboxy-4,7-dichlorofluorescein ("5- and 6-HEX")

To a 1-liter Erlenmeyer flask equipped with a magnetic stirring bar was added 5- or 6-TET (6.3 g) and 1M carbonate/bicarbonate buffer at pH 9.4 (60 mL). Household bleach (sodium hypochlorite, 50 mL) was added dropwise over 20 minutes. The progress of the reaction was monitored by reverse phase HPLC. A total of 67 mL of bleach was added. The solution was acidified with concentrated HCl (15 mL) and extracted with ethyl acetate (100 mL). The organic phase was concentrated to a bright yellow solid (7.3 g). $^1$H NMR (DMSO-$d_6$) δ8.1 (1H); 7.4 (2H).

We claim:

1. In a method of detecting a plurality of electrophoretically separated DNA fragments, the improvement comprising labelling at least one of the DNA fragments with a 4,7-dichlorofluorescein dye.

2. The method of claim 1 wherein said 4,7-dichlorofluorescein dye is defined by the formula:

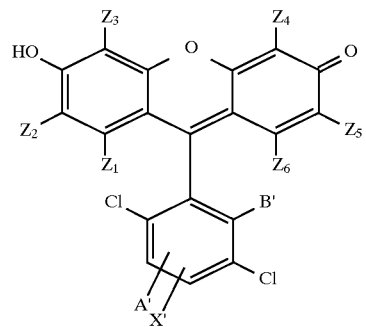

wherein:

A' is hydrogen, fluoro, chloro, a linking functionality, or a group that may be converted to a linking functionality;

B' is fluoro, chloro, or an acidic anionic group;

X' is hydrogen, fluoro, or chloro;

$Z_1$ is hydrogen or, when taken with $Z_2$, benzo;

$Z_2$, when taken alone, is hydrogen, halo, lower alkyl, lower alkyloxy, a linking functionality, or a group that may be converted to a linking functionality, or when taken with $Z_1$, benzo;

$Z_3$ and $Z_4$ are separately hydrogen, halo, lower alkyl, lower alkyloxy, a linking functionality, or a group that may be converted to a linking functionality;

$Z_5$, when taken alone, is hydrogen, halo, lower alkyl, lower alkyloxy, a linking functionality, or a group that may be converted to a linking functionality, or when taken with $Z_6$, benzo;

$Z_6$ is hydrogen or, when taken with $Z_5$, benzo; and wherein at least one of A, $Z_2$, $Z_3$, $Z_4$, and $Z_5$ is a linking functionality or a group that may be converted to a linking functionality.

3. The method of claim 2 wherein:

A' is carboxyl, sulfonyl, isothiocyanate, succinimidyl carboxylate, phosphoramidite, or amino;

B' is carboxyl or sulfonyl;

X' is hydrogen or chloro;

$Z_2$, when taken alone, is hydrogen, methyl, ethyl, methoxy, ethoxy, or chloro;

$Z_3$, and $Z_4$ are separately hydrogen, methyl, ethyl, methoxy, ethoxy, chloro, carboxyl, sulfonyl, isothiocyanate, succinimidyl carboxylate, phosphoramidite, or methylamino;

$Z_5$, when taken alone, is hydrogen, methyl, ethyl, methoxy, ethoxy, or chloro; and wherein only one of A', $Z_3$, and $Z_4$ is carboxyl, sulfonyl, methylamino, isothiocyanate, succinimidyl carboxylate, phosphoramidite, or amino.

4. The method of claim 3 wherein $Z_3$, and $Z_4$ are separately hydrogen, methyl, ethyl, methoxy, ethoxy, or chloro.

5. The method of claim 4 wherein $Z_2$, when taken alone, is hydrogen, methoxy, ethoxy, or chloro;

$Z_3$, and $Z_4$ are separately hydrogen, methoxy, ethoxy, chloro; and $Z_5$, when taken alone, is hydrogen, methoxy, ethoxy, or chloro.

6. The method of claim 5 wherein B' is carboxy and A' is carboxy, succinimidyl carboxylate, or phosphoramidite.

* * * * *

UNITED STATES PATENT AND TRADEMARK OFFICE
CERTIFICATE OF CORRECTION

PATENT NO. : 5,885,778
DATED : March 23, 1999
INVENTOR(S) : Menchen et al.

It is certified that error appears in the above-identified patent and that said Letters Patent is hereby corrected as shown below:

Column 1,
Line 43, delete " 35Smith" and insert therefor -- Smith --.

Column 3,
Line 62, delete "4,7-chloro" and insert therefor -- 4,7-dichloro --.

Column 5,
Line 1, delete "$Z_6$" and insert therefor -- $Z_5$ --.

Column 7,
Line 14, delete "concetrating" and insert therefor -- concentrating --.

Column 10,
Line 57, delete " 3,3" and insert therefor-- 3.3 --.
Line 58, delete "6,4" and insert therefor -- 6.4 --.

Columns 10 through Column 13,
Delete every occurrence of "Example [Roman numeral]" and insert therefor -- Example [the corresponding alphanumeric character] --.

Column 10,
Line 67 through Column 11, line 2, delete every occurrence of "ul" and substitute there for -- µl --.

Column 12,
Lines 33 and 34, delete every occurrence of "ul" and substitute therefor -- µl --.

Column 14, claim 2,
Formula II set forth in lines 27-40 and also in Col. 14, line 46, delete "B'" and substitute therefor -- D' --.
Line 62, delete "A" and substitute therefor -- A' --.

UNITED STATES PATENT AND TRADEMARK OFFICE
CERTIFICATE OF CORRECTION

PATENT NO. : 5,885,778
DATED : March 23, 1999
INVENTOR(S) : Menchen et al.

It is certified that error appears in the above-identified patent and that said Letters Patent is hereby corrected as shown below:

Column 15, claim 3,
Line 1, delete "B'" and substitute therefor -- D' --.

Column 16, claim 6,
Line 11, delete "B'" and substitute therefor -- D' --

Signed and Sealed this

Eighteenth Day of December, 2001

Attest:

Attesting Officer

JAMES E. ROGAN
Director of the United States Patent and Trademark Office